(12) United States Patent
Brinson et al.

(10) Patent No.: US 8,852,545 B2
(45) Date of Patent: Oct. 7, 2014

(54) PROCESS FOR RECOVERY OF HIGH BOILING WASTE

(75) Inventors: Jonathan Ashley Brinson, Shanghai (CN); William Patrick Brady, Crestwood, KY (US)

(73) Assignee: Dow Corning Corporation, Midland, MI (US)

( * ) Notice: Subject to any disclaimer, the term of this patent is extended or adjusted under 35 U.S.C. 154(b) by 713 days.

(21) Appl. No.: 13/143,134

(22) PCT Filed: Jun. 30, 2009

(86) PCT No.: PCT/US2009/049190
§ 371 (c)(1),
(2), (4) Date: Jul. 1, 2011

(87) PCT Pub. No.: WO2010/085274
PCT Pub. Date: Jul. 29, 2010

(65) Prior Publication Data
US 2011/0268641 A1  Nov. 3, 2011

(30) Foreign Application Priority Data
Jan. 22, 2009 (CN) .......................... 2009 1 0126726

(51) Int. Cl.
*C01B 33/08* (2006.01)
*C07F 7/12* (2006.01)

(52) U.S. Cl.
CPC ................ *C07F 7/126* (2013.01); *C07F 7/128* (2013.01)

USPC .......................................... 423/342; 423/341

(58) Field of Classification Search
USPC ................................................. 423/342, 341
See application file for complete search history.

(56) References Cited

U.S. PATENT DOCUMENTS

| | | |
|---|---|---|
| 4,059,608 A | 11/1977 | Calas et al. |
| 4,393,229 A | 7/1983 | Ritzer et al. |
| 4,962,219 A | 10/1990 | Halm et al. |
| 5,175,329 A | 12/1992 | Bokerman et al. |
| 5,292,909 A | 3/1994 | Chadwick et al. |
| 5,292,912 A | 3/1994 | Chadwick et al. |
| 5,321,147 A | 6/1994 | Chadwick et al. |
| 5,326,896 A | 7/1994 | Chadwick et al. |
| 5,430,168 A | 7/1995 | Ferguson et al. |
| 5,606,090 A | 2/1997 | Brinson et al. |
| 5,627,298 A | 5/1997 | Freeburne et al. |
| 5,629,438 A | 5/1997 | Freeburne et al. |
| 5,907,050 A | 5/1999 | Crum et al. |
| 5,922,894 A | 7/1999 | Crum et al. |
| 6,013,235 A | 1/2000 | Brinson et al. |
| 6,013,824 A | 1/2000 | Wood |

FOREIGN PATENT DOCUMENTS

| | | |
|---|---|---|
| EP | 0564109 | 1/1998 |
| EP | 0634418 | 12/2001 |
| EP | 0812851 | 11/2002 |
| WO | 2010065287 | 6/2010 |

*Primary Examiner* — Edward Johnson
(74) *Attorney, Agent, or Firm* — Catherine U. Brown

(57) ABSTRACT

Waste streams from different chloromonosilane production processes are combined and reacted in a single recovery process. Useful monosilane species may be obtained with a single recovery process.

14 Claims, No Drawings

PROCESS FOR RECOVERY OF HIGH BOILING WASTE

CROSS-REFERENCE TO RELATED APPLICATIONS

This application is a U.S. national stage filing under 35 U.S.C. §371 of PCT Application No. PCT/US09/49190 filed on Jun. 30, 2009, currently pending, which claims the benefit of Chinese Patent Application No. 200910126726.9 filed Jan. 22, 2009, under 35 U.S.C. §119 (a)-(d) and 35 U.S.C. §365(a). PCT Application No. PCT/US09/49190 and Patent Application No. 200910126726.9 are hereby incorporated by reference.

BACKGROUND OF THE INVENTION

High boiling silicon compounds, such as compounds having Si—Si linkages, Si—O—Si linkages, or Si—$C_a$—Si linkages (where subscript a is 1 or more), in their molecules are formed as the undesirable by-products of industrial processes that produce monosilanes as chemical intermediates. For purposes of this application, the term 'monosilane' refers to a silane species having one silicon atom with four substituents bonded thereto. Monosilanes include, but are not limited to, trichlorosilane ($HSiCl_3$), silicon tetrachloride ($SiCl_4$), dimethyldichlorosilane (($CH_3)_2SiCl_2$), dimethylhydrogenchlorosilane (($CH_3)_2HSiCl$), methylhydrogendichlorosilane ($CH_3HSiCl_2$), and methyltrichlorosilane ($CH_3SiCl_3$). The term 'high boiling polymers' refers to compounds having more than one silicon atom, and they are exemplified by the high boiling silicon compounds described above. The high boiling polymers have boiling points above the boiling points of the chloromonosilanes, e.g., 70° C. and above, alternatively 80° C. and above. High boiling polymers are present in residues produced as waste streams from industrial processes for making chloromonosilanes and methylchloromonosilanes (e.g., the direct process). High boiling polymers are also present in residues produced in industrial processes for making silicon (e.g., processes for making solar grade silicon and/or semiconductor grade polycrystalline silicon). The term 'residue' refers to any stream containing the high boiling polymers.

In an industrial process for making chloromonosilanes, hydrogen chloride (HCl) is reacted with metallurgical grade silicon (Si) in an uncatalyzed reaction system to produce trichlorosilane ($HSiCl_3$). Another process involves reaction of methyl chloride with metallurgical grade Si in a system catalyzed with copper compounds and promoted with a number of various metal additives such as zinc, tin and phosphorous to form methylchloromonosilanes (MCS). A portion of the silicon and chloride (in the form of HCl from the $HSiCl_3$ process or $CH_3Cl$ from the MCS process) in the initial reaction and in downstream processes is lost to the formation of by-product high boiling polymers.

The $HSiCl_3$ process residue may comprise disilanes of the formula $H_bSi_2Cl_{(6-b)}$, where subscript b has a value ranging from 0 to 6, alternatively 0 to 4; and disiloxanes of formula $H_cSi_2OCl_{(6-c)}$, where subscript c has a value ranging from 0 to 6. In the $HSiCl_3$ process, these high boiling polymers include tetrachlorodisiloxane ($HCl_2SiOSiCl_2H$, $H_2Si_2OCl_4$), pentachlorodisiloxane ($HCl_2SiOSiCl_3$, $HSi_2OCl_5$), hexachlorodisiloxane ($Cl_3SiOSiCl_3$, $Si_2OCl_6$), hexachlorodisilane ($Si_2Cl_6$), pentachlorodisilane ($HSi_2Cl_5$), tetrachlorodisilane ($H_2Si_2Cl_4$), and trichlorodisilane ($H_3Si_2Cl_3$).

The MCS process residue may comprise disilanes of the formula $Me_dSi_2Cl_{(6-d)}$, where subscript d has a value ranging from 0 to 6 and disiloxanes and/or silalkanediyl compounds of formula $Me_eSi_2XCl_{(6-e)}$, where subscript e has a value ranging from 0 to 6, and X is an oxygen atom or an divalent hydrocarbon group group. In the MCS process, these high boiling polymers include $Si_2Cl_6$, tetramethyldichlorodisilane ($Me_4Si_2Cl_2$), trimethyltrichlorodisilane ($Me_3Si_2Cl_3$), tetramethyltetrachlorotrisilane ($Me_4Si_3Cl_4$), tetramethyldichlorodisilmethylene ($Me_2ClSiCH_2SiMe_2Cl$), trimethyltrichlorodisilmethylene ($Me_2ClSiCH_2SiMeCl_2$), trimethyltrichlorodisilethylene ($Me_2ClSi(CH_2)_2SiMeCl_2$), trimethyltrichlorodisilpropylene ($Me_2ClSi(CH_2)_3SiMeCl_2$), $Me_2ClSiCH_2Si(Me)(Cl)SiMeCl_2$, $Me_2ClSiCH_2Si(Me)(Cl)CH_2SiMeCl_2$, and trimethyltrichlorodisiloxane ($Me_3Si_2OCl_3$); where Me represents a methyl group.

The high boiling polymers, such as the disilanes, from the $HSiCl_3$ and MCS processes can be recovered and converted to useful monosilanes via hydrogenation, chlorination or hydrochlorination, but catalysts may be required to make the reactions economical. In the MCS system, the most economically favorable system is the hydrogenation of methylchlorodisilanes with the use of in-situ catalysts in the process residue, which contains the high boiling polymers. MCS process residue can be prepared for downstream processing so it is rich with in-situ catalysts valuable for hydrogenation. In the $HSiCl_3$ process, the $HSiCl_3$ process residue containing the high boiling polymers is typically disposed of by quenching and/or incineration.

BRIEF SUMMARY OF THE INVENTION

A process comprises: 1) combining a first process residue that contains a catalytic amount of an in-situ catalyst and a second process residue that does not contain a catalytic amount of an in-situ catalyst; and 2) reacting a high boiling polymer in the product of step 1).

DETAILED DESCRIPTION OF THE INVENTION

For purposes of this application, the process will be described with respect to a MCS process residue that contains a catalytic amount of an in-situ catalyst and a $HSiCl_3$ process residue that does not contain a catalytic amount of an in-situ catalyst. However, this disclosure is exemplary and not limiting of the scope of the invention set forth in the claims. One skilled in the art would recognize that variations of the process may be practiced, including but not limited to, using a different residue for the first process residue that contains a catalytic amount of an in-situ catalyst and/or the second process residue that does not contain a catalytic amount of an in-situ catalyst. For example, a silicon process residue (e.g., from a chemical vapor deposition process for the production of solar grade silicon or semiconductor grade polycrystalline silicon) may be used as the second process residue instead of the $HSiCl_3$ process residue when the silicon process residue does not contain a catalytic amount of an in-situ catalyst. Alternatively, an alkylhalomonosilane process may be used to produce the first process residue that contains a catalytic amount of an in-situ catalyst, where the alkyl group may be a group other than methyl, e.g., ethyl or propyl, and/or the halogen atom may be other than chlorine, e.g., bromine, fluorine, or iodine.

A process for converting the high boiling polymers described above to useful monosilanes comprises:

a) combining $HSiCl_3$ process residue and MCS process residue to form a high boiling residue;

b) contacting the high boiling residue with hydrogen gas. Step b) may be performed in a reactor by heating the high boiling residue, the hydrogen gas, and any additional reactant (if added) to a temperature ranging from 150° C. to 1000° C. at a pressure ranging from 345 kPa to 68,900 kPa for a residence time of 1 second to 5 hours, thereby producing a product comprising a monosilane.

This process may provide the advantage of a catalyst being present in-situ in the MCS process residue, where the catalyst is useful for obtaining monosilanes from both the MCS process residue and the $HSiCl_3$ process residue. Without wishing to be bound by theory, it is thought that the catalyst may be more soluble in the MCS process residue than the $HSiCl_3$ process residue, therefore, better catalytic activity with respect to $HSiCl_3$ process residue may be achieved when the $HSiCl_3$ process residue and MCS process residue are combined. The catalyst promotes the formation of monosilane from the high boiling polymer in the high boiling residue. The catalyst may promote redistribution of alkyl and halogen between silicon atoms (and/or redistribution of hydrogen and halogen between silicon atoms). The catalyst may promote hydrogenation, scission of silicon-silicon bonds, scission of silicon-carbon bonds, and/or scission of silicon-oxygen bonds. To achieve these reactions, one or more catalytic species providing the above described activities may be used for the catalyst.

A Lewis Acid or its equivalent may be used to provide redistribution activity to the catalyst. Examples of catalytic species useful to effect redistribution include aluminum trichloride, antimony pentachloride, zirconium tetrachloride, potassium aluminum tetrachloride, quaternary phosphonium halide, quaternary ammonium halide, ammonium halide, cuprous chloride, boric acid, and boron halide. Suitable redistribution catalysts are known in the art and are disclosed in, for example, U.S. Pat. Nos. 4,393,229 and 5,175,329.

Suitable catalytic species for hydrogenation include aluminum trichloride; antimony pentachloride; a copper species such as cuprous chloride, copper (Cu) metal, Cu salts, and complexes of Cu salts with organic ligands; a nickel species such as nickel (Ni) metal, supported Ni, organometallic Ni compounds, complexed Ni salts, and inorganic Ni compounds; a palladium species such as palladium (Pd) metal, supported Pd, organometallic Pd compounds, complexed Pd salts, and inorganic Pd compounds; a platinum species such as platinum (Pt) metal, supported Pt, organometallic Pt compounds, complexed Pt salts, and inorganic Pt compounds; and combinations thereof. The supported Ni, supported Pd, supported Pt may be supported on alumina, carbon, silica, or zeolite. For example, Pd on carbon and Pt on aluminua are examples of supported catalysts. Hydrogenation catalysts are known in the art and are disclosed in, for example, U.S. Pat. Nos. 5,175,329; 5,292,909; 5,292,912; 5,321,147; 5,326,896; and 5,627,298. Without wishing to be bound by theory, it is thought that the catalytic species present in-situ in the MCS process residue (e.g., copper species) can be used to catalyze a hydrochlorination reaction of HCl and the high boiling polymers from the $HSiCl_3$ process residue, as well as the high boiling polymers from the MCS process residue.

The catalytic species described above may also promote scission of silicon-silicon bonds, optionally silicon-carbon bonds, and optionally silicon-oxygen bonds. Therefore, it may be unnecessary to add additional catalytic species to the catalyst to promote formation of monosilanes from high boiling silicon compounds. The amount of catalyst is sufficient to catalyze at least one of the hydrogenation, redistribution, and scission reactions described above. The exact amount depends on various factors including the reaction to be catalyzed, the composition of the high boiling residue, and the monosilane product desired. The catalytic species may be formed in-situ in, for example, the MCS process, the catalytic species may be added to the high boiling residue, or both. The amount of catalyst (either in-situ, added, or a combination thereof) may range from 0.01 to 20% of catalyst based on the weight of high boiling residue, alternatively 0.5 to 5% on the same basis. All amounts, ratios, and percentages in this application are by weight, unless otherwise indicated. One skilled in the art would recognize that aluminum trichloride may be added to the high boiling residue or may be formed in-situ by materials that form aluminum trichloride. All or a portion of the aluminum trichloride may be formed in-situ during performance of the $HSiCl_3$ process and the MCS process, and the isolation of the monosilane fractions therefrom, to form the high boiling residue. Aluminum trichloride is useful for catalyzing hydrogenation, redistribution, and scission reaction.

The $HSiCl_3$ process residue may result from the stripping or distillation of the reaction product of HCl and Si metalloid. The $HSiCl_3$ process residue may be combined directly with MCS process residue. Alternatively, the $HSiCl_3$ process residue may be pretreated before step a). Pretreating can include an additional step of stripping or distilling to remove all or a portion of $HSiCl_3$ and/or $SiCl_4$ from the $HSiCl_3$ process residue before step a), pretreating can include filtering to remove solids, or both. The $HSiCl_3$ process residue may comprise disilanes of the formula $H_bSi_2Cl_{(6-b)}$, where subscript b has a value ranging from 0 to 6, alternatively 0 to 4; and disiloxanes of formula $H_cSi_2OCl_{(6-c)}$, where subscript c has a value ranging from 0 to 6. The disilanes are exemplified by $Si_2Cl_6$, $HSi_2Cl_5$, $H_2Si_2Cl_4$, and $H_3Si_2Cl_3$. The disiloxanes are exemplified by $H_2Si_2OCl_4$, $HSi_2OCl_5$, and $Si_2OCl_6$. The $HSiCl_3$ process residue may comprise 0 to 15% $H_2Si_2OCl_4$, 5% to 35% $HSi_2OCl_5$, 15% to 25% $Si_2OCl_6$, and 35% to 75% $Si_2Cl_6$, based on the combined weights of the disilanes and disiloxanes in the $HSiCl_3$ process residue. $HSiCl_3$ process residue may further comprise solids, which are insoluble in the high boiling polymers described above. For example, the solids may be polychlorosiloxanes having 4 or more silicon atoms and higher order polychlorosilanes. The solids may further comprise silicon particulates. Alternatively, after pretreatment the $HSiCl_3$ process residue may comprise 68% of the disilanes, 31% of the disiloxanes; 0.5% other high boiling silicon compounds; and 0.5% solid particulate containing silicon. Before pretreating, the $HSiCl_3$ process residue may comprise up to 75% of chloromonosilanes such as $HSiCl_3$ and $SiCl_4$ and up to 30% solid particulate containing silicon with the balance being the high boiling polymers and other high boiling silicon compounds described above. Examples of the $HSiCl_3$ process residue that may be used in the process described herein are disclosed, for example, in U.S. Pat. No. 6,013,235 and U.S. Provisional Patent Application Ser. No. 61/119,391.

The MCS process residue may comprise disilanes of the formula $Me_dSi_2Cl_{(6-d)}$, where subscript d has a value ranging from 0 to 6 and disiloxanes and/or silalkanediyls of formula $Me_eSi_2XCl_{(6-e)}$, where subscript e has a value ranging from 0 to 6, and X is an oxygen atom or an divalent hydrocarbon group group. The MCS process residue may comprise $Si_2Cl_6$, $Me_4Si_2Cl_2$, $Me_3Si_2Cl_3$, $Me_4Si_3Cl_4$, $Me_2ClSiCH_2SiMe_2Cl$, $Me_2ClSiCH_2SiMeCl_2$, $Me_2ClSi(CH_2)_2SiMeCl_2$, $Me_2ClSi(CH_2)_3SiMeCl_2$, $Me_2ClSiCH_2Si(Me)(Cl)SiMeCl_2$, $Me_2ClSiCH_2Si(Me)(Cl)CH_2SiMeCl_2$, and $Me_3Si_2OCl_3$. The exact amount of each species present in the MCS process residue may vary depending on the MCS process conditions, however, the MCS process residue may comprise 50% to 60% of the disilanes and 15% to 25% of the silalkylenes as well as in-situ catalysts, solids containing silicon, and other metals. An example of MCS process residue may comprise 0 to 4%

Me$_3$SiCl, 0 to 2% MeHSiCl$_2$, 0 to 5% EtMeSiCl$_2$, 0 to 5% PrMeSiCl$_2$, 0% to 9% Me$_4$Si$_2$Cl$_2$, 5 to 40% Me$_3$Si$_2$Cl$_3$, 15 to 54% MeCl$_2$Si$_2$MeCl$_2$, 0 to 9% Me$_2$ClSiCH$_2$SiClMe$_2$, 0% to 15% Me$_2$ClSiCH$_2$SiCl$_2$Me, 0 to 20% MeCl$_2$SiCH$_2$SiCl$_2$Me, 0 to 5% MeCl$_2$SiOSiCl$_2$Me, 9% to 26% other high boiling species and 0 to 40% solids, with the proviso that the total adds up to 100%, and where Et represents an ethyl group and Pr represents a propyl group.

Examples of the MCS process residue that may be used in the process described herein are disclosed, for example, in U.S. Pat. Nos. 5,175,329; 5,430,168; 5,606,090; 5,627,298; 5,629,438; 5,907,050; 5,922,894; and 6,013,824.

The amount of HSiCl$_3$ process residue combined with MCS process residue to produce the high boiling residue used in the process described above is greater than 0, and the exact amount will depend on various factors including the compositions of both process residues, whether the residue is pre-treated, and the in-situ catalyst present in the MCS process residue, and whether any additional catalyst is added. However, the amount of HSiCl$_3$ process residue may range from greater than 0 to 100 weight parts HSiCl$_3$ process residue, per 100 weight parts MCS process residue; alternatively 5 weight parts to 100 weight parts HSiCl$_3$ process residue, alternatively 5 weight parts to 50 weight parts, and alternatively 5 weight parts to 10 weight parts of HSiCl$_3$ process residue; per 100 weight parts MCS process residue. The high boiling residue for use in the process may have a boiling point of 70° C. or above, alternatively 80° C. or above.

The process may be run in any conventional pressurizable reactor suitable for contact with chlorosilanes. The process may be run as a batch process or as a continuous process. The process may be run, for example, in continuous stirred tank reactor, a bubble-column reactor, a trickle-bed reactor, or a plug flow reactor.

The process conditions will depend on various factors including the composition of the high boiling residue and the monosilane desired to be produced. However, the pressure inside the reactor may range from 345 kPa to 68,900 kPa, alternatively 689 to 34,475 kPa, alternatively 1,000 kPa to 15,000 kPa, alternatively 2,000 kPa to 10,500 kPa, and alternatively 4,000 to 8,000 kPa. The temperature inside the reactor may range from 150° C. to 1000° C., alternatively 150° C. to 400° C., alternatively 200° C. to 500° C., alternatively 200° C. to 250° C., alternatively 215° C. to 280° C., alternatively 235° C. to 245° C., alternatively 275° C. to 500° C., and alternatively 300° C. to 350° C. Without wishing to be bound by theory, it is thought pressure and temperature can be varied to affect the monosilanes formed. For example, when pressure with lower limit greater than 250 psig (1725 kPa) and temperature ranging from 150° C. to 500° C., alternatively 250° C. to 400° C., and alternatively 320° C. to 380° C. is used, the reaction may favor dimethyldichlorosilane instead of methyltrichlorosilane. Residence time at these temperatures and pressures depends on various factors including the type of reactor selected, exact temperature and pressure therein, and the amounts and types of catalytic species present, however, residence time may range from one second to five hours.

The amount of hydrogen gas added to the reactor is not critical and can be any amount sufficient to effect a desired level of hydrogenation. However, the amount may range from 0.05 to 10%, alternatively 1 to 5%, hydrogen gas, based on the weight of the high boiling residue. Optionally, the reactor may be supplemented with an additional reactant. The additional reactant may be a chlorine-rich species, for example HCl, HSiCl$_3$, SiCl$_4$, CH$_3$SiCl$_3$, CH$_3$Cl, or a combination thereof (alternatively HSiCl$_3$, SiCl$_4$, Si$_2$Cl$_6$, or a combination thereof); or a SiH-functional species, such as HSiCl$_3$ or CH$_3$HSiCl$_2$; an alkyl-rich species such as tetramethylsilane (SiMe$_4$), trimethylchlorosilane (Me$_3$SiCl), dimethyldichlorosilane (Me$_2$SiCl$_2$), or a combination thereof; or a combination of different chlorine-rich species, SiH functional species, and/or alkyl-rich species. The additional reactant selected, if any, will depend on various factors including the monosilanes desired to be produced, e.g., after the scission and/or redistribution and/or hydrogenation reactions. Without wishing to be bound by theory, it is thought that supplementing with a chlorine-rich species may redistribute more Cl onto the disilanes and polysilanes and make them easier to scise and/or control the distribution of monosilanes in the product to favor commercially more useful species. One skilled in the art would be able to select appropriate reactants and process conditions described to and/or control the distribution of monosilanes using the processes described in, for example, U.S. Pat. Nos. 5,175,329; 5,292,912; 5,321,147; 5,606,090; and 5,907,050. Alternatively, supplementing with an alkyl-rich species may produce a monosilane enriched in alkyl groups such as methyl, using the reactants and process conditions described, for example, in U.S. Pat. Nos. 4,962,219; and 6,013,824. One skilled in the art would be able to select appropriate temperature and pressure conditions and any additional reactants without undue experimentation to achieve the monosilane species desired in the product.

One skilled in the art would recognize when selecting ingredients for the chlorine-rich species, the SiH-functional species, and the alkyl-rich species that there may be overlap among them, for example, when a monosilane having more than one of a chlorine atom, a hydrogen atom, and an alkyl group bonded to the silicon atom is used. One skilled in the art would be able to distinguish among and select appropriate species to supplement the reactant based on various factors including the monosilane desired to be produced.

The process described above may further comprise step c), recovering one or more monosilane species from the product of step b). Step c) may be performed by separation using conventional methods for separating liquid mixtures, for example distillation. The monosilane species may include HSiCl$_3$, SiCl$_4$, (CH$_3$)$_2$SiCl$_2$, CH$_3$HSiCl$_2$, and (CH$_3$)$_2$HSiCl.

EXAMPLE

The following example is included to demonstrate the invention. However, those of ordinary skill in the art should, in light of the present disclosure, appreciate that many changes can be made in the specific embodiments which are disclosed and still obtain a like or similar result without departing from the spirit and scope of the invention set forth in the claims.

A stream of HSiCl$_3$ process residue contained: 30 vol % solids with balance being a liquid made up of 13.6% HSiCl$_3$, 73.9% SiCl$_4$, 0.3% HCl$_2$SiOSiCl$_2$H, 6.9% HCl$_2$SiOSiCl$_3$, 3.6% Cl$_3$SiOSiCl$_3$, 1.5% Si$_2$Cl$_6$, and 0.2% other uncharacterized high boiling species.

A total of 5 weight parts of HSiCl$_3$ process residue was combined with 60 weight parts of MCS process residue from a process to form a high boiling residue. The residues were combined, filtered to reduce solids content to 5% or less, and fed over a 15 day period to a hydrogenation reactor at a feed rate of 0.4 parts by weight per hour. The reactor temperature ranged from 200° C. to 250° C., and the reactor pressure ranged from 56 to 58 barg (5,600 to 5,800 kPa). The residence time of the high boiling residue in the reactor was 2 to 5 hours.

INDUSTRIAL APPLICABILITY

The process described herein combines wastes from the HSiCl$_3$ process and the MCS process in a single, one-step technique. The process may provide the advantage of reduced capital costs required for two separate $HSiCl_3$ and MCS recovery processes, and it has the advantage of using the in-situ catalysts (such as the copper species described above) of the MCS system to catalyze the reaction of high boiling polymers from the $HSiCl_3$ to produce useful $HSiCl_3$ and/or $SiCl_4$, as well as useful methylchloromonosilanes.

The invention claimed is:

1. A process comprising:
   a) combining a first process residue that contains compounds having more than one silicon atom and that contains a catalytic amount of an in-situ catalyst and a second process residue that contains compounds having more than one silicon atom and that does not contain a catalytic amount of an in-situ catalyst, where the second process residue is in an amount of at least 5 weight parts of the second process residue, per 100 weight parts of the first process residue; and
   b) contacting the product of step a) with hydrogen gas, thereby producing a product comprising a monosilane.

2. The process of claim 1, where the first process residue is a methylchloromonosilane process residue.

3. The process of claim 1, where the second process residue is a $HSiCl_3$ process residue.

4. The process of claim 1, where the second process residue is a silicon process residue.

5. The process of claim 1, further comprising pretreating the second process residue before step a).

6. The process of claim 1, further comprising c) recovering one or more monosilanes from the product, where the monosilanes are selected from the group consisting of $HSiCl_3$, $SiCl_4$, $(CH_3)_2SiCl_2$, $CH_3HSiCl_2$, and $(CH_3)_2HSiCl$.

7. The process of claim 1, where the process is performed in a reactor operating at a temperature ranging from 150° C. to 1000° C.

8. The process of claim 1, where the process is performed in a reactor operating at a pressure ranging from 345 to 68,900 kPa.

9. The process of claim 1, where the residence time in the reactor ranges from 1 second to 5 hours.

10. The process of claim 1, further comprising supplementing with a reactant selected from the group consisting of a chlorine-rich species, a SiH-functional species, an alkyl-rich species, and a combination thereof.

11. The process of claim 1, further comprising supplementing with a chlorine-rich species selected from the group consisting of $HSiCl_3$, $SiCl_4$, $Si_2Cl_6$, and a combination thereof.

12. The process of claim 1, where the first process residue is a methylchloromonosilane process residue and where the methylchloromonosilane process residue contains a copper species, and the process further comprises supplementing with HCl.

13. The process of claim 1, further comprising supplementing with a SiH-functional species selected from the group consisting of $HSiCl_3$, $CH_3HSiCl_2$, and a combination thereof.

14. The process of claim 1, further comprising supplementing with an alkyl-rich species selected from the group consisting of tetramethylsilane, trimethylchlorosilane, dimethyldichlorosilane, and a combination thereof.

* * * * *